US007758566B2

(12) United States Patent
Simpson et al.

(10) Patent No.: US 7,758,566 B2
(45) Date of Patent: Jul. 20, 2010

(54) VALVE ASSEMBLY

(75) Inventors: Philip J. Simpson, Escondido, CA (US); Walter D. Gillespie, San Diego, CA (US); David G. Matsuura, Encinitas, CA (US)

(73) Assignee: ICU Medical, Inc., San Clemente, CA (US)

( * ) Notice: Subject to any disclaimer, the term of this patent is extended or adjusted under 35 U.S.C. 154(b) by 303 days.

(21) Appl. No.: 10/584,920

(22) PCT Filed: Dec. 21, 2004

(86) PCT No.: PCT/US2004/042723

§ 371 (c)(1),
(2), (4) Date: Dec. 28, 2006

(87) PCT Pub. No.: WO2005/065767

PCT Pub. Date: Jul. 21, 2005

(65) Prior Publication Data

US 2007/0120083 A1    May 31, 2007

Related U.S. Application Data

(60) Provisional application No. 60/532,916, filed on Dec. 30, 2003.

(51) Int. Cl.
*A61M 25/16* (2006.01)
(52) U.S. Cl. ..................................... 604/537
(58) Field of Classification Search ........... 604/246, 604/247, 249, 256, 533, 534, 535, 537, 905, 604/536; 251/149.1, 149.6
See application file for complete search history.

(56) References Cited

U.S. PATENT DOCUMENTS

| 2,842,382 A | 7/1958 | Franck |
| 2,931,668 A | 4/1960 | Baley |
| 2,968,497 A | 1/1961 | Treleman |
| 3,127,892 A | 4/1964 | Bellamy, Jr. et al. |

(Continued)

FOREIGN PATENT DOCUMENTS

EP    0 791 371 A1    8/1997

(Continued)

OTHER PUBLICATIONS

International Search Report and written Opinion of International Application No. PCT/US2004/042723 mailed on Sep. 9, 2004 in 5 pages.

(Continued)

*Primary Examiner*—Kevin C Sirmons
*Assistant Examiner*—Kami A Bosworth
(74) *Attorney, Agent, or Firm*—Knobbe Martens Olson & Bear LLP

(57) ABSTRACT

Disclosed herein is a valve assembly comprising a male luer end portion and a female luer end portion and a passage for the transfer of fluids extending between the male and female luer end portions, valve means movable between a first position, in which the passage is closed, and a second position, in which the passage is open, biasing means for biasing the valve means toward the first position, and actuating means extending into the male luer end portion and coupled to the valve means to actuate the valve means when a female luer end portion of a medical accessory is engaged with the male luer end portion.

19 Claims, 15 Drawing Sheets

U.S. PATENT DOCUMENTS

| | | |
|---|---|---|
| 3,304,047 A | 2/1967 | Martin |
| 3,334,860 A | 8/1967 | Bolton, Jr. |
| 3,707,972 A | 1/1973 | Villari et al. |
| 3,729,031 A | 4/1973 | Baldwin |
| 3,986,508 A | 10/1976 | Barrington |
| 4,055,179 A | 10/1977 | Manschot et al. |
| 4,066,067 A | 1/1978 | Micheli |
| 4,076,285 A | 2/1978 | Martinez |
| 4,080,965 A | 3/1978 | Phillips |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,195,632 A | 4/1980 | Parker et al. |
| 4,233,982 A | 11/1980 | Bauer et al. |
| 4,245,635 A | 1/1981 | Kontos |
| 4,324,239 A | 4/1982 | Gordon et al. |
| 4,334,551 A | 6/1982 | Pfister |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,430,073 A | 2/1984 | Bemis et al. |
| 4,436,125 A | 3/1984 | Blenkush |
| 4,457,749 A | 7/1984 | Bellotti et al. |
| 4,511,359 A | 4/1985 | Vaillancourt |
| 4,538,836 A | 9/1985 | Krutten |
| 4,610,469 A | 9/1986 | Wolff-Mooij |
| 4,619,640 A | 10/1986 | Potolsky et al. |
| 4,623,332 A | 11/1986 | Lindmayer et al. |
| 4,629,159 A | 12/1986 | Wellenstam |
| 4,660,803 A | 4/1987 | Johnston et al. |
| 4,662,878 A | 5/1987 | Lindmayer |
| 4,700,744 A | 10/1987 | Rutter et al. |
| 4,723,603 A | 2/1988 | Plummer |
| 4,728,075 A | 3/1988 | Paradis |
| 4,745,950 A | 5/1988 | Mathieu |
| 4,774,964 A | 10/1988 | Bonaldo |
| 4,774,965 A | 10/1988 | Rodriguez et al. |
| 4,781,702 A | 11/1988 | Herrli |
| 4,804,015 A | 2/1989 | Albinsson |
| 4,816,024 A | 3/1989 | Sitar et al. |
| 4,834,271 A | 5/1989 | Litwin |
| 4,862,913 A | 9/1989 | Wildfang |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |
| 4,950,260 A | 8/1990 | Bonaldo |
| D313,277 S | 12/1990 | Haining |
| D314,050 S | 1/1991 | Sone |
| 5,006,114 A | 4/1991 | Rogers et al. |
| 5,021,059 A | 6/1991 | Kensey et al. |
| 5,047,021 A | 9/1991 | Utterberg |
| 5,065,783 A | 11/1991 | Ogle, II |
| 5,070,885 A | 12/1991 | Bonaldo |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,242,393 A | 9/1993 | Brimhall et al. |
| 5,242,425 A | 9/1993 | White et al. |
| 6,242,393 B1 | 9/1993 | Brimnall |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,324,270 A | 6/1994 | Kayan et al. |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,391,150 A | 2/1995 | Richmond |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,826 A | 4/1995 | Molnar et al. |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,464,399 A | 11/1995 | Boettger |
| 5,470,319 A | 11/1995 | Mayer |
| 5,470,327 A | 11/1995 | Helgren et al. |
| 5,474,536 A | 12/1995 | Bonaldo |
| 5,480,393 A | 1/1996 | Bommarito |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,527,284 A | 6/1996 | Ohnemus et al. |
| 5,533,708 A | 7/1996 | Atkinson et al. |
| 5,533,983 A | 7/1996 | Haining |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A * | 11/1996 | Patzer ........................ 604/249 |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,129 A | 4/1997 | Mayer |
| 5,616,130 A | 4/1997 | Mayer |
| RE35,539 E | 6/1997 | Bonaldo |

| | | |
|---|---|---|
| 5,643,224 A | 7/1997 | Szapiro et al. |
| 5,645,538 A | 7/1997 | Richmond |
| 5,674,206 A | 10/1997 | Allton et al. |
| 5,676,346 A | 10/1997 | Leinsing |
| 5,685,866 A | 11/1997 | Lopez |
| 5,699,821 A | 12/1997 | Paradis |
| 5,700,248 A | 12/1997 | Lopez |
| 5,735,826 A | 4/1998 | Richmond |
| 5,738,144 A | 4/1998 | Rogers |
| 5,749,861 A | 5/1998 | Guala et al. |
| RE35,841 E | 7/1998 | Frank et al. |
| 5,782,816 A | 7/1998 | Werschmidt et al. |
| 5,785,693 A | 7/1998 | Haining |
| 5,806,831 A | 9/1998 | Paradis |
| 5,814,024 A | 9/1998 | Thompson et al. |
| 5,820,601 A | 10/1998 | Mayer |
| 5,839,715 A | 11/1998 | Leinsing |
| 5,848,994 A | 12/1998 | Richmond |
| 5,947,954 A | 9/1999 | Bonaldo |
| 6,029,946 A | 2/2000 | Doyle |
| 6,036,171 A | 3/2000 | Weinheimer et al. |
| 6,050,978 A | 4/2000 | Orr et al. |
| 6,063,062 A | 5/2000 | Paradis |
| 6,068,011 A | 5/2000 | Paradis |
| 6,068,617 A | 5/2000 | Richmond |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,152,913 A | 11/2000 | Feith et al. |
| 6,206,860 B1 | 3/2001 | Richmond |
| 6,224,578 B1 | 5/2001 | Davis et al. |
| 6,245,048 B1 | 6/2001 | Fangrow et al. |
| 6,299,132 B1 | 10/2001 | Weinheimer et al. |
| 6,428,520 B1 | 8/2002 | Lopez |
| 6,431,219 B1 | 8/2002 | Redler et al. |
| 6,485,472 B1 | 11/2002 | Richmond |
| 6,499,719 B1 | 12/2002 | Clancy et al. |
| 6,508,792 B2 | 1/2003 | Szames et al. |
| 6,541,802 B2 | 4/2003 | Doyle |
| 6,543,745 B1 | 4/2003 | Enerson |
| 6,581,906 B2 | 6/2003 | Pott et al. |
| 6,595,964 B2 | 7/2003 | Finley et al. |
| 6,595,981 B2 | 7/2003 | Huet |
| 6,609,696 B2 | 8/2003 | Enerson |
| 6,666,852 B2 | 12/2003 | Niedospial, Jr. |
| 6,695,817 B1 | 2/2004 | Fangrow |
| 6,745,998 B2 | 6/2004 | Doyle |
| 6,840,501 B2 | 1/2005 | Doyle |
| 6,875,205 B2 | 4/2005 | Leinsing |
| 6,899,315 B2 | 5/2005 | Maiville et al. |
| 6,955,669 B2 | 10/2005 | Curutcharry |
| 6,964,406 B2 | 11/2005 | Doyle |
| 7,004,934 B2 | 2/2006 | Vaillancourt |
| 7,037,302 B2 | 5/2006 | Vaillancourt |
| 7,040,598 B2 | 5/2006 | Raybuck |
| 7,044,441 B2 | 5/2006 | Doyle |
| 7,100,891 B2 | 9/2006 | Doyle |
| 7,125,396 B2 | 10/2006 | Leinsing et al. |
| 7,140,592 B2 | 11/2006 | Phillips |
| 7,182,313 B2 | 2/2007 | Doyle |
| 7,195,228 B2 | 3/2007 | Tiberghien et al. |
| 7,244,249 B2 | 7/2007 | Leinsing et al. |
| 7,306,198 B2 | 12/2007 | Doyle |
| 7,306,566 B2 | 12/2007 | Raybuck |
| 7,347,458 B2 | 3/2008 | Rome et al. |
| 7,350,764 B2 | 4/2008 | Raybuck |
| 7,497,484 B2 | 3/2009 | Ziman |
| 2001/0029355 A1 | 10/2001 | Szames et al. |
| 2002/0066715 A1 | 6/2002 | Niedospial, Jr. |
| 2003/0060804 A1 | 3/2003 | Vaillancourt |
| 2003/0111623 A1 | 6/2003 | Enerson |
| 2003/0136932 A1 | 7/2003 | Doyle |
| 2003/0208165 A1 | 11/2003 | Christensen et al. |
| 2004/0124389 A1* | 7/2004 | Phillips .................. 251/149.4 |
| 2005/0015075 A1* | 1/2005 | Wright et al. ............... 604/535 |
| 2005/0124942 A1 | 6/2005 | Richmond |
| 2005/0212292 A1 | 9/2005 | Parrino et al. |
| 2005/0228362 A1 | 10/2005 | Vaillancourt |
| 2005/0245872 A1 | 11/2005 | Simpson et al. |
| 2006/0058734 A1 | 3/2006 | Phillips |
| 2006/0129109 A1 | 6/2006 | Shaw et al. |
| 2006/0142730 A1 | 6/2006 | Proulx et al. |
| 2006/0142735 A1 | 6/2006 | Whitley |
| 2006/0149213 A1 | 7/2006 | Raybuck |
| 2006/0192164 A1 | 8/2006 | Korogi et al. |
| 2006/0202146 A1 | 9/2006 | Doyle |
| 2006/0253084 A1 | 11/2006 | Nordgren |
| 2007/0017583 A1 | 1/2007 | Fangrow, Jr. |
| 2007/0043334 A1 | 2/2007 | Guala |
| 2007/0073270 A1 | 3/2007 | Christensen et al. |
| 2007/0088292 A1 | 4/2007 | Fangrow, Jr. |
| 2007/0088293 A1 | 4/2007 | Fangrow, Jr. |
| 2007/0088294 A1 | 4/2007 | Fangrow, Jr. |
| 2007/0088324 A1 | 4/2007 | Fangrow, Jr. |
| 2007/0088325 A1 | 4/2007 | Fangrow, Jr. |
| 2007/0088327 A1 | 4/2007 | Guala |
| 2007/0179453 A1 | 8/2007 | Lim et al. |
| 2008/0103485 A1 | 5/2008 | Kruger |
| 2008/0287920 A1 | 11/2008 | Fangrow et al. |

FOREIGN PATENT DOCUMENTS

| | | |
|---|---|---|
| GB | 2 353 078 | 2/2001 |
| WO | 01/03756 A1 | 1/2001 |
| WO | WO 01/03756 | 1/2001 |
| WO | 2004/060474 A1 | 7/2004 |

OTHER PUBLICATIONS

U.S. Appl. No. 11/417,923, filed May 3, 2006, including file history.
U.S. Appl. No. 11/417,882, filed May 3, 2006, including file history.
U.S. Appl. No. 11/417,671, filed May 3, 2006, including file history.
U.S. Appl. No. 11/417,648, filed May 3, 2006, including file history.
U.S. Appl. No. 11/417,909, filed May 3, 2006, including file history.
U.S. Appl. No. 11/417,882, filed May 3, 2006, including file history.
International Search Report dated Jun. 28, 2005.
Written Opinion of the International Searching Authority dated Jun. 28, 2005.
U.S. Appl. No. 11/417,923, filed May 3, 2006, Thomas F. Fangrow.
U.S. Appl. No. 11/417,671, filed May 3, 2006, Thomas F. Fangrow.
U.S. Appl. No. 11/417,648, filed May 3, 2006, Thomas F. Fangrow.
U.S. Appl. No. 11/417,909, filed May 3, 2006, Thomas F. Fangrow.
U.S. Appl. No. 11/417,882, filed May 3, 2006, Thomas F. Fangrow.
International Written Opinion of International Application No. PCT/US2004/042723 issued on Jul. 3, 2006 in 10 pages.
Malaysian Examination and Search Report dated Mar. 14, 2008 regarding App. No. PI 20045404, in 3 pages.

* cited by examiner

30

VALVE ASSEMBLY

This application is a national stage application filed under 35 U.S.C. 371 based on International Application No. PCT/US04/42723 filed Dec. 21, 2004 which claims benefit of U.S. Provisional Application No. 60/532,916 filed Dec. 30, 2003.

BACKGROUND OF THE INVENTION

1. Field of the Invention

The present invention relates to medical fluid delivery valves and more particularly to valve assemblies for use with syringes or other medical dispensing devices.

2. Description of the Related Art

Syringes are commonly used to deliver medications and other biological fluids to a patient. The syringe typically has a plunger which is sealingly engaged with an outer cylindrical chamber to form an inner fluid—receiving chamber. A 'male' luer fitting is usually provided at a delivery end of the chamber which receives a female luer fitting with a needle assembly or the like. The fluid channel joining the cavity to the luer fitting is usually open, so that when the needle is removed, the cavity is open to the environment. This is problematic since many medications and biological fluids are sensitive (or can degrade when exposed) to the environment.

It is therefore an object of the present invention to provide a novel valve assembly for use with a syringe or other medical dispensing devices, enabling the latter to be closed to the environment when in an unattached condition.

SUMMARY OF THE INVENTION

In one of its aspects, the present invention provides a valve assembly comprising a male luer end portion, a female luer end portion and a channel for the transfer of fluids between the male and female luer end portions, valve means movable between a closed position and an open position, biasing means for biasing the valve means toward the closed position, and actuating means extending into the male luer end portion and coupled to the valve means to actuate the valve means when a female luer end portion of a medical accessory is coupled with the male luer end portion.

In an embodiment the male luer end portion has an inner projection and outer threaded sheath which is spaced therefrom to receive the female luer end portion therebetween. The actuating means includes an actuating member positioned between the outer threaded sheath and the inner projection.

In an embodiment, the valve means includes a valve seat and a valve member moveable relative thereto. The channel includes a first channel portion adjacent the female luer end portion and the inner projection includes a second channel portion. The valve member has a valve channel portion in fluid communication with the first and second channel portions. The valve seat is formed in the second channel portion and the valve member is integrally formed with the female luer end portion.

In one embodiment, the valve member includes an anchor flange extending outwardly toward an inner surface of the housing portion. In this case, the housing portion is coupled to the male luer end portion for movement therewith relative to the valve member. The male luer end portion engages the anchor flange when the valve means is in the closed position and the male luer end portion is spaced from said anchor flange when the valve means is in the open position. The housing portion terminates at an end region adjacent the female luer end portion, the biasing means includes a compression spring located within the housing between the end region and the outer anchor flange.

In another of its aspects, the present invention provides a medical dispensing device comprising a body having a chamber therein to contain a fluid material, a valve assembly in fluid communication with the chamber, the valve assembly having a male coupling member for engaging a female coupling member on a medical accessory to form a fluid coupling between the medical dispensing device and the medical accessory, the valve assembly further comprising flow control means operable to control fluid flow through the male coupling member, the flow control means being operable to be displaced by the female coupling member to open the male coupling member when female coupling member is operatively connected therewith, the flow control means being operable to be displaced by the female coupling member to close the male coupling member when the female coupling member is disconnected therefrom.

In one embodiment, the male coupling member includes an inner male portion and an outer sheath portion spaced therefrom to form a passage there between for receiving the female coupling member, the flow control means including at least one valve actuating portion positioned in the passage to abut the female coupling member and to displace the valve member during the travel of the female coupling member along the passage. The valve assembly includes a valve member and a valve seat, wherein the valve member is positioned against the seat to close the male coupling member. The valve actuating portion includes a pair of abutment elements which are spaced from one another along the passage to receive the female coupling member there between, wherein the pair of abutment elements are operable to travel with the female coupling member along the passage.

In one embodiment, the actuating portion is longitudinally oriented relative to the passage and the abutment elements are positioned along the actuating portion.

The valve member includes a back plate and a plurality of actuating portions equally spaced on the back plate, each of the actuating portions having first and second abutment elements.

In one embodiment, the valve actuating portion includes a locking flange which is adjacent one of the abutment elements. The valve assembly includes a locking seat to receive the locking flange when the male coupling member is in the closed position. The actuating portion has a distal end region, the locking flange being located adjacent the distal end region and the locking seat is formed in the outer sheath portion. The actuating portion is thus arranged to flex in order to displace the locking flange from the locking seat.

In yet another aspect, the present invention provides a medical dispensing device comprising a body having a chamber therein to contain a fluid material, a valve assembly in fluid communication with the chamber, the valve assembly having a male coupling member for engaging a female coupling member on a medical accessory to form a fluid coupling between the medical dispensing device and the medical accessory, the male coupling member including a projection and an outer valve member movable relative to the projection, the projection and the outer valve member forming a fluid channel there between, a sheath portion encircling the projection and spaced therefrom to form a passage to receive the female coupling member, the valve member being engageable with the female coupling member and movable relative to the projection to open the fluid channel when the female coupling member is connected with the male coupling member.

In one embodiment, the valve member forms an outer surface of the male coupling portion.

In an embodiment, biasing means is provided to bias the valve member toward an engaged position with the projection to close the fluid channel. In this particular case, the passage ends at an inner wall and the biasing means includes a spring located between the inner wall and the valve member.

In one embodiment, the projection is fixed to the body and includes an inner passage, the inner passage having one end which is open to the chamber and another end which is open to the fluid channel. The projection also includes an enlarged end portion, the valve member including an outer portion arranged to engage the enlarged end portion to close the fluid channel. In this case the enlarged end portion and the outer end portion on the valve member have mating bevelled surfaces.

In one embodiment, the female coupling member has a leading segment, the valve member being dimensioned to fit within the leading segment.

Preferably, the medical dispensing device includes such items as a syringe, an IV bottle, an IV line, a powder and/or atomized fluid and/or gas inhalant dispenser, an implant delivery dispenser, a ventilator, a syringe pump, an intubation tube, a gastrointestinal feeding tube or a plurality and/or a combination thereof.

Preferably, the medical material is in solid, liquid or gaseous form or a combination thereof and has beneficial properties to enhance life, to promote health, to cure and/or treat a disease, condition or ailment, to monitor and/or indicate a bodily function or a combination thereof. For example, the medical material may be useful for, among others, IV therapy, implantation, stem cell therapy, oncology therapy, blood transfusion and/or organ transplantation.

BRIEF DESCRIPTION OF THE DRAWINGS

Several preferred embodiments of the present invention will now be described, by way of example only, with reference to the appended drawings in which.

DESCRIPTION OF THE PREFERRED EMBODIMENTS

Figure 1:
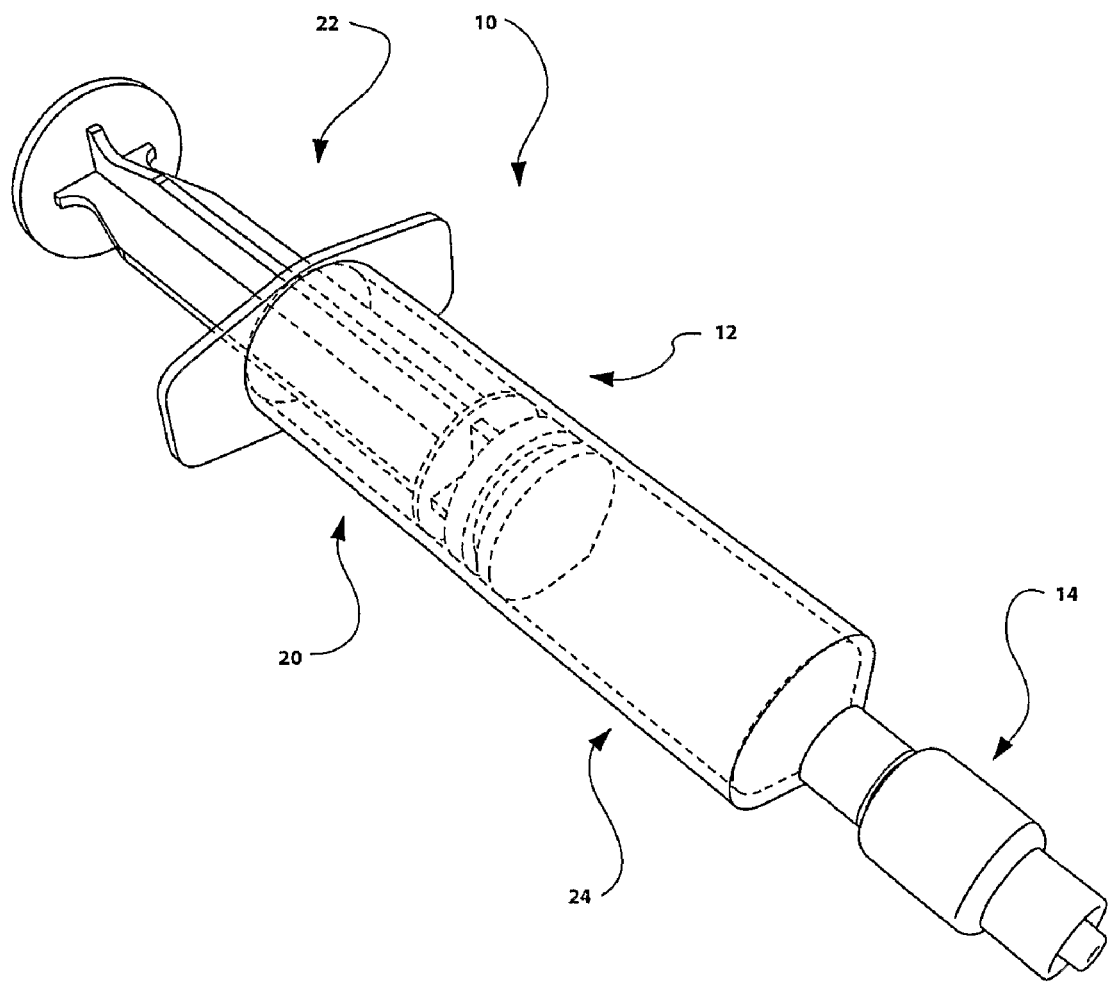
FIG. 1 is a perspective view of a syringe assembly.
Figure 2:
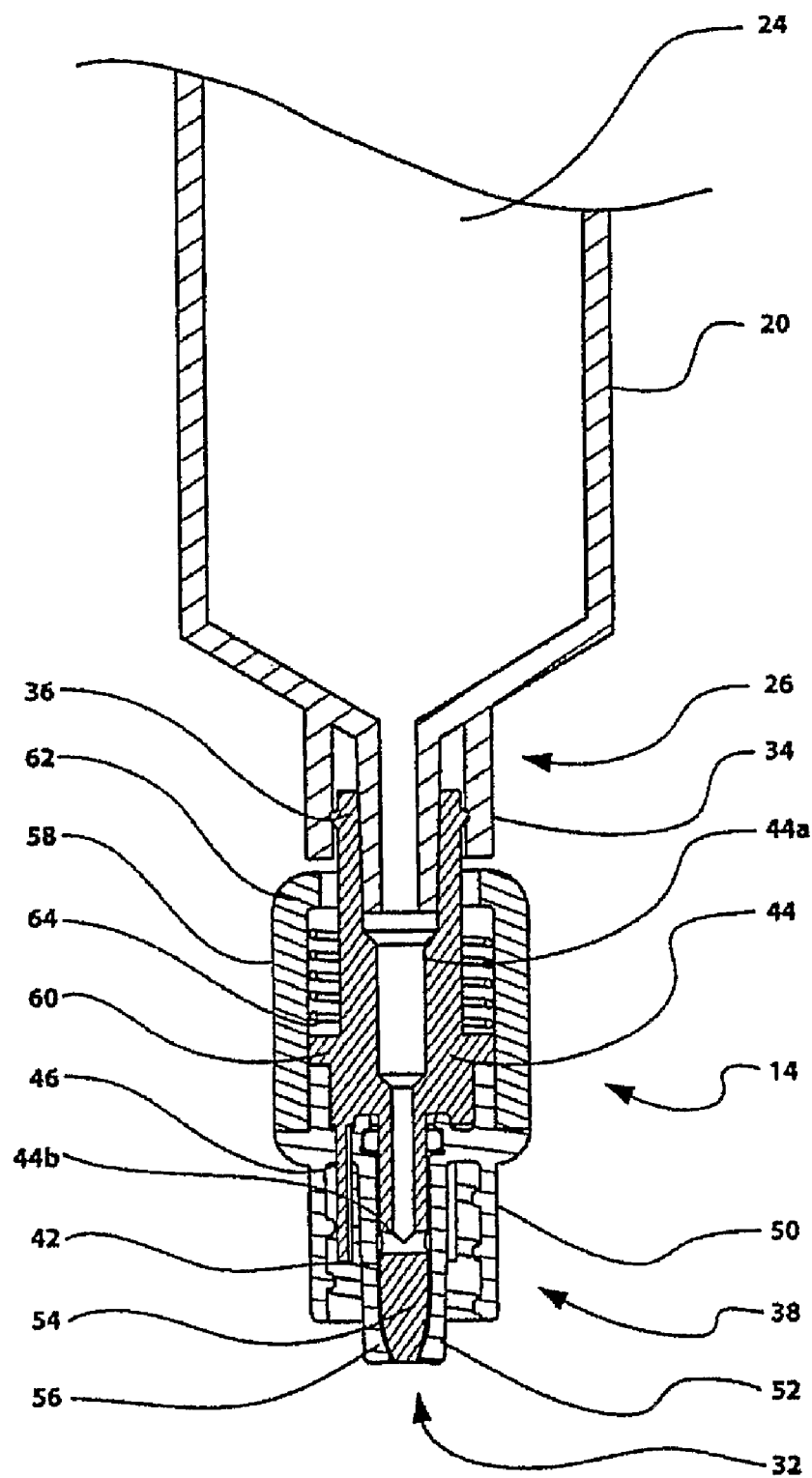
FIG. 2 is a sectional view of a portion of the assembly of FIG. 1.
Figure 3:
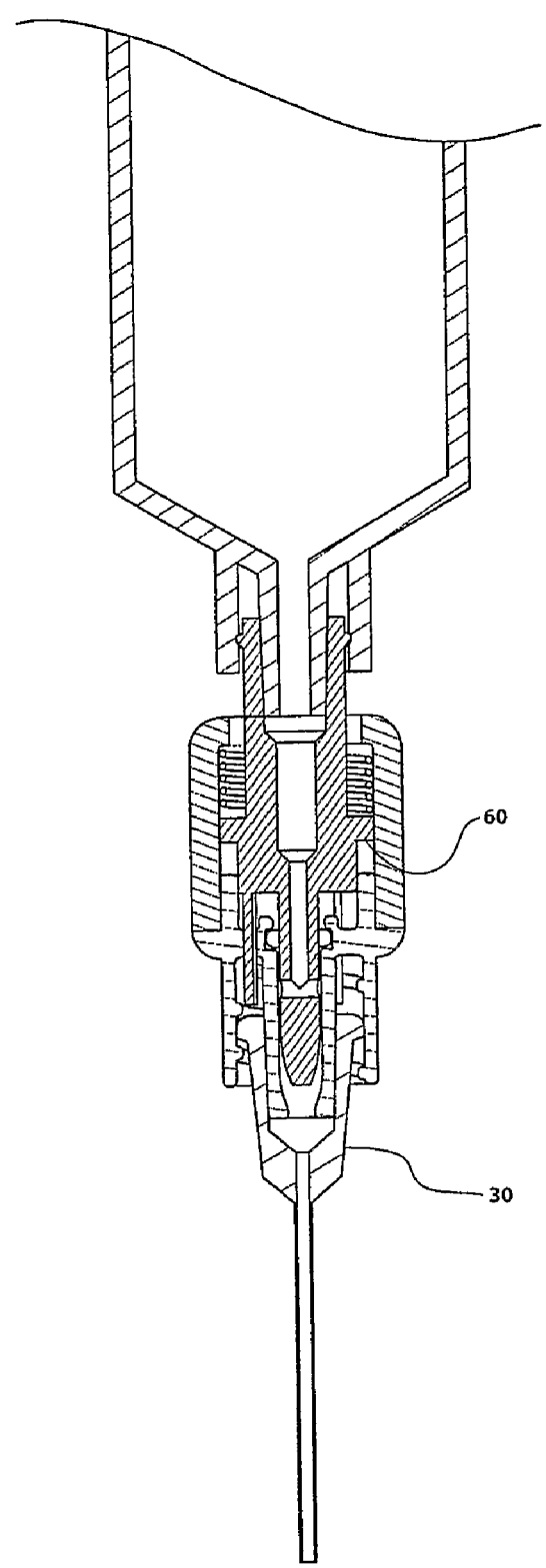
FIGS. 3 and 4 are sectional views of the assembly of FIG. 1 in two alternate operative positions.
Figure 4:
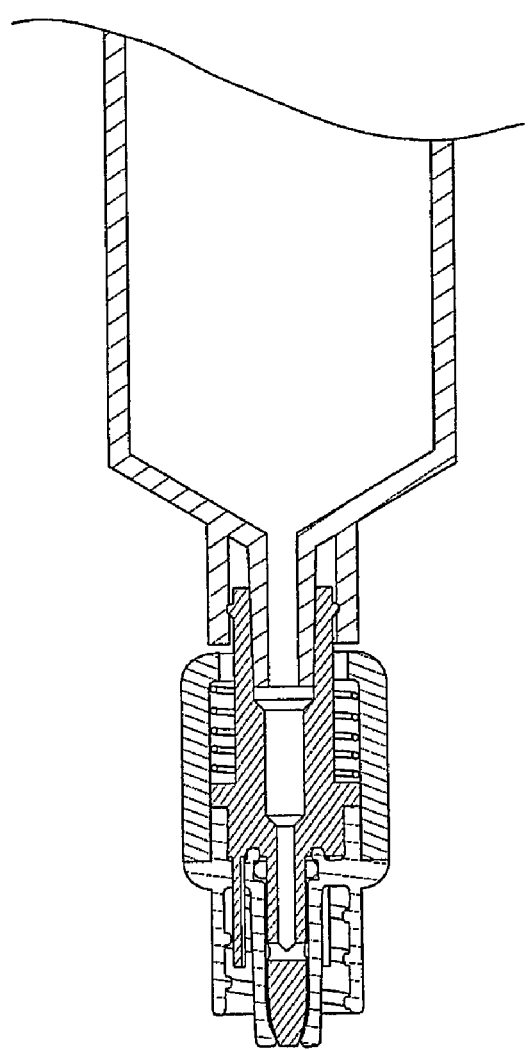
Figure 4:
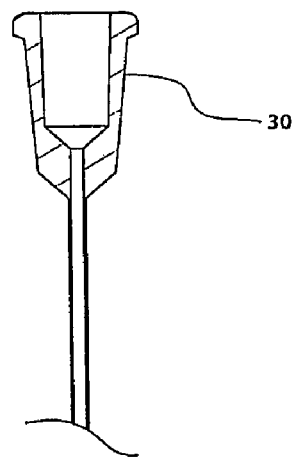

Referring to the figures, and in particular FIG. 1, there is provided a syringe assembly 10 comprising a syringe 12 and a valve unit 14. The syringe 12 has a chamber 20 containing a plunger 22 to form a cavity 24. Referring to FIG. 2, the cavity has an outlet 26 and the valve unit 14 is located downstream of the outlet 26 for coupling the cavity 24 with a medical accessory such as a needle 30 (as shown in FIGS. 3 and 4). The valve unit 14 has an outlet 32 and flow control means, as will be described, to control fluid flow through the outlet, the flow control means being operable to open the outlet when the coupling section is operatively connected with the medical accessory, the flow control means being operable to close the outlet when the valve unit is disconnected from the medical accessory and to remain closed until connected once again with a medical accessory.

In this case, the chamber 20 includes a first male luer end portion 34 adjacent the outlet 26 and the valve unit 14 includes a first female luer end portion 36 which is engageable with the male luer end portion 34. The valve unit 14 also includes a second male luer end portion 38 for coupling with the medical accessory 30.

Although the chamber 20 and the valve unit 14 are separate from one another in this case, it will be understood that they may, alternatively, be integrally formed, for example by combining the first male luer end portion 34 with the female luer end portion 36.

The valve unit 14 has a channel 42 for the transfer of fluids between the female and male luer end portions 36, 38. A valve means, in the form of a valve member 44 is located in the valve unit 14 and is movable between a first position (as shown in FIG. 2), in which the channel is closed, and a second position (as shown in FIG. 3), in which the channel is open. An actuating means, in the form of an actuating member 46 (shown in FIG. 2), extends outwardly from the valve member 44 and into the male luer end portion 38. The actuating member 46 is coupled to the valve member 44 to actuate it when a female luer end portion of the medical accessory 30 is engaged with the male luer end portion 38.

In the embodiment of FIGS. 1 to 4, the male luer end portion 38 has an outer threaded sheath 50 which is spaced from an inner projection 52. In this case, the actuating member 46 is positioned between the outer threaded sheath 50 and the inner projection 52. The valve member 44 includes a valve plug portion 54 moveable relative to a valve seat portion 56. The valve member 44 has an upper end which is integrally formed with the female luer end portion 36. An outer housing member 58 is slidably mounted on the valve member 44. In this case, the outer housing member 58 is joined to the male luer end portion 38. The valve member 44 also has a valve channel 44a extending from the female luer end portion 36 to the valve plug portion 42 where it terminates at one or more transverse flow openings 44b to join with the channel 42.

The valve member 44 includes an anchor flange 60, and the male luer end portion 38 seats, directly or indirectly, against the anchor flange 60 when the valve is in the closed position as viewed in FIG. 2. Conversely, the male luer end portion 38 is spaced from said anchor flange when the valve is in the open position as shown in FIG. 3.

The outer housing 58 terminates at a radially inwardly directed end region 62 adjacent the female luer end portion 34 and a biasing means in the form of a compression spring 64 is located within the outer housing between the end region 62 and the anchor flange 60 to bias the valve member toward the first position to close the valve unit.

Figure 5:
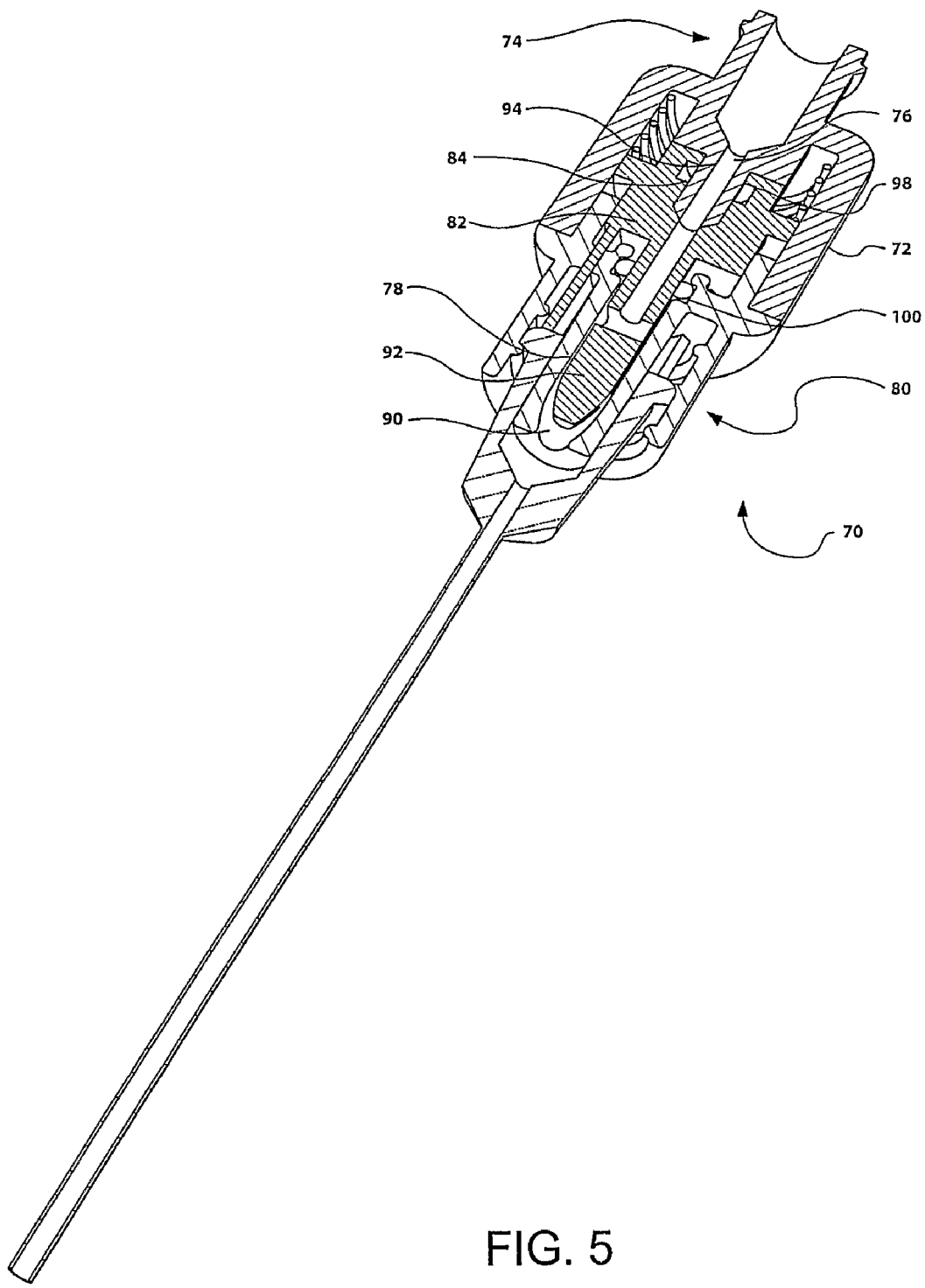
FIG. 5 is a fragmentary sectional perspective view of a portion of another syringe assembly.

An alternative arrangement is shown in FIG. 5. In this case, the valve unit 70 has a housing 72 which is integrally formed with the female luer end portion 74. A first channel portion 76 is adjacent the female luer end portion 74 and a second channel portion 78 is adjacent a male luer end portion 80. In this case, the valve means includes a valve member 82 having a valve channel 84 in fluid communication with the first and second channel portions 76 and 78. In this case, the valve seat portion is formed at 90 in the second channel portion 78.

The valve member 82 includes a plug portion 92 which is movable relative to and within the second channel portion 78 for engaging the seat portion 90 to close the second channel portion 78. The first channel portion 76 includes a tubular projection 94 extending from the female luer end portion 74. In this case, the valve channel 84 in the valve member 82 is coextensive with the first and second channel portions 76, 78. In this case, the tubular projection 94 is slidably engaged with the valve member 82 within the valve channel 84 and sealed therein by way of seal 98. Likewise, the valve member 84 is sealed within the second channel portion 78 by way of seal 100.

The syringe assembly 10 is used as follows. First, the valve unit 14 is joined to the syringe 12 by engaging the corresponding first male luer end portion 34 with the female luer end portion 36. In this condition, the second male luer end portion 38 is unattached with a medical accessory such as the needle 30 and the actuator 46 is fully extended into the second male luer end portion 38 as shown in FIG. 2. Consequently, the valve member 44 is biased to its closed position, thereby engaging the valve plug portion 54 against the valve seat 56.

The needle 30 is then attached to the syringe by engaging the female luer end portion on the needle 30 with the second male luer end portion 38. Doing so causes the female luer end portion on the needle 30 to abut and displace the actuating member 46, thereby causing the valve member 44 to be displaced upwardly (as viewed in FIG. 2) thereby releasing the valve plug portion 54 from its sealed abutment with the valve seat 56 to open the valve channel. The plunger 22 may then be displaced outwardly to cause fluids in the proximity of the pointed end of the needle 30 to be drawn into the cavity 24, by a path starting at the valve seat 56 through the channel 42 to the transverse flow openings 44b, to the valve channel 44a and on through the female luer end portion and into the cavity 24. The needle 30 may then be removed causing the actuating member 46 to be displaced downwardly (as viewed in FIG. 2) causing the immediate displacement of the valve plug portion to abut the seat 56 and thereby close the valve.

Another device is shown at 120 FIGS. 6 to 12, having a body 122 forming an inner chamber 124 therein to contain a fluid material. A valve assembly 126 is in fluid communication with the chamber 124 and has a male coupling member 128 for engaging a female coupling member 130 on a medical accessory (in this case a needle 132) to form a fluid coupling between the device 120 and the needle 132.

The valve assembly 126 is operable to control fluid flow through the male coupling member 128 and more particularly to be in an open position when the male coupling member 128 is operatively connected with the female coupling member 130 and, conversely, to be in a closed position when the male coupling member 128 is disconnected from the female coupling member 130.

Figure 8:
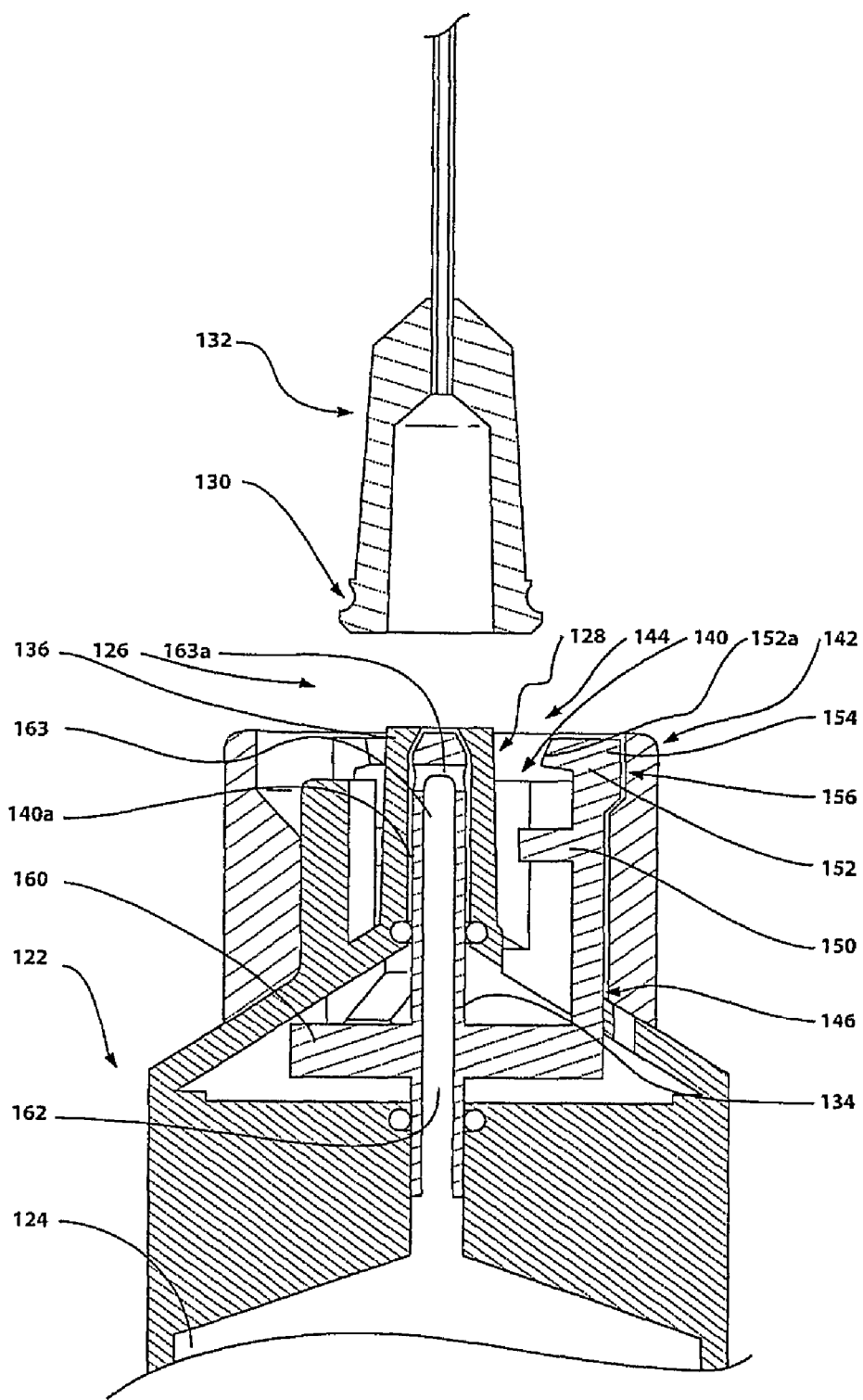
FIGS. 8 to 12 are fragmentary sectional views of the syringe assembly of FIG. 6.

In this case, the body 122 and the valve assembly 126 are integrally formed and, as seen in FIG. 8, the latter includes a valve member 134 and a valve seat 136. The valve member 134 is shown in its position against the valve seat 136 to close the male coupling member 128, but for a very minor gap there between for illustrative purposes only.

The male coupling member 128 includes an inner male portion 140 having an inner fluid channel 140a and an outer sheath portion 142 spaced from the inner male portion 140 to form a passage 144 there between for receiving the female coupling member 130. At least one, in this case three, valve actuating portions 146 (two being shown in FIG. 7) are positioned in the passage 144 to abut the female coupling member 130 and to displace the valve member during the travel of the female coupling member 130 along the passage 144. In this case, each valve actuating portion 146 is integrally formed with the valve member 134.

Each valve actuating portion 146 includes a pair of abutment elements 150, 152 which are spaced from one another along the passage 144 to receive the female coupling member 130 there between and to travel with the female coupling member along the passage 144. The abutment element 152 has a bevelled outer surface 152a for reasons to be described. Each actuating portion 146 is longitudinally oriented relative to the passage 144 and the abutment elements 150, 152 are positioned along the actuating portion 146.

Each valve actuating portion 146 includes a locking flange 154 and the valve assembly includes a locking seat 156 to receive the locking flange 154 when the valve member 134 is in the closed position. In this case, the actuating portion 146 has a distal end region and the locking flange 154 is located in the distal end region, while the locking seat 156 is formed in the outer sheath portion 142.

Figure 10:
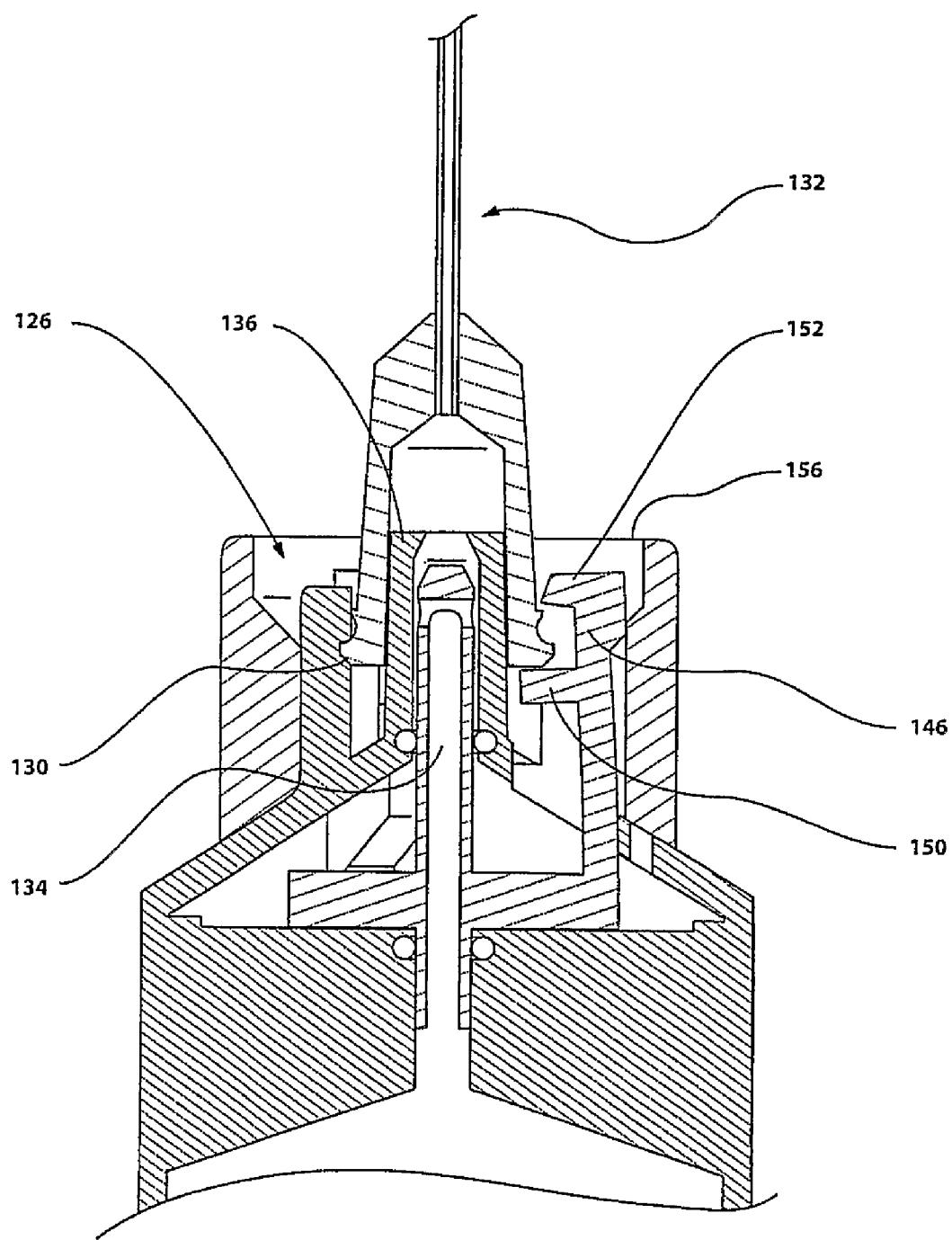

It will be seen in FIG. 10 that each actuating portion 146 is arranged to flex in order to displace the locking flange 154 out of the locking seat 156.

Referring to FIG. 8, the valve member 134 includes a back plate 160 and the actuating portions 146 are equally spaced on the back plate 160. The back plate 160 has a central fluid channel 162 which is in fluid communication with the chamber 124 and the valve member 134 has a fluid channel 163 therein in fluid communication with the central fluid channel 162 and hence the chamber 124. In addition, the fluid channel 163 has a lateral portion 163a which establishes fluid communication between the fluid channel 163 and an inner fluid channel 140a in the inner male portion.

Figure 9:
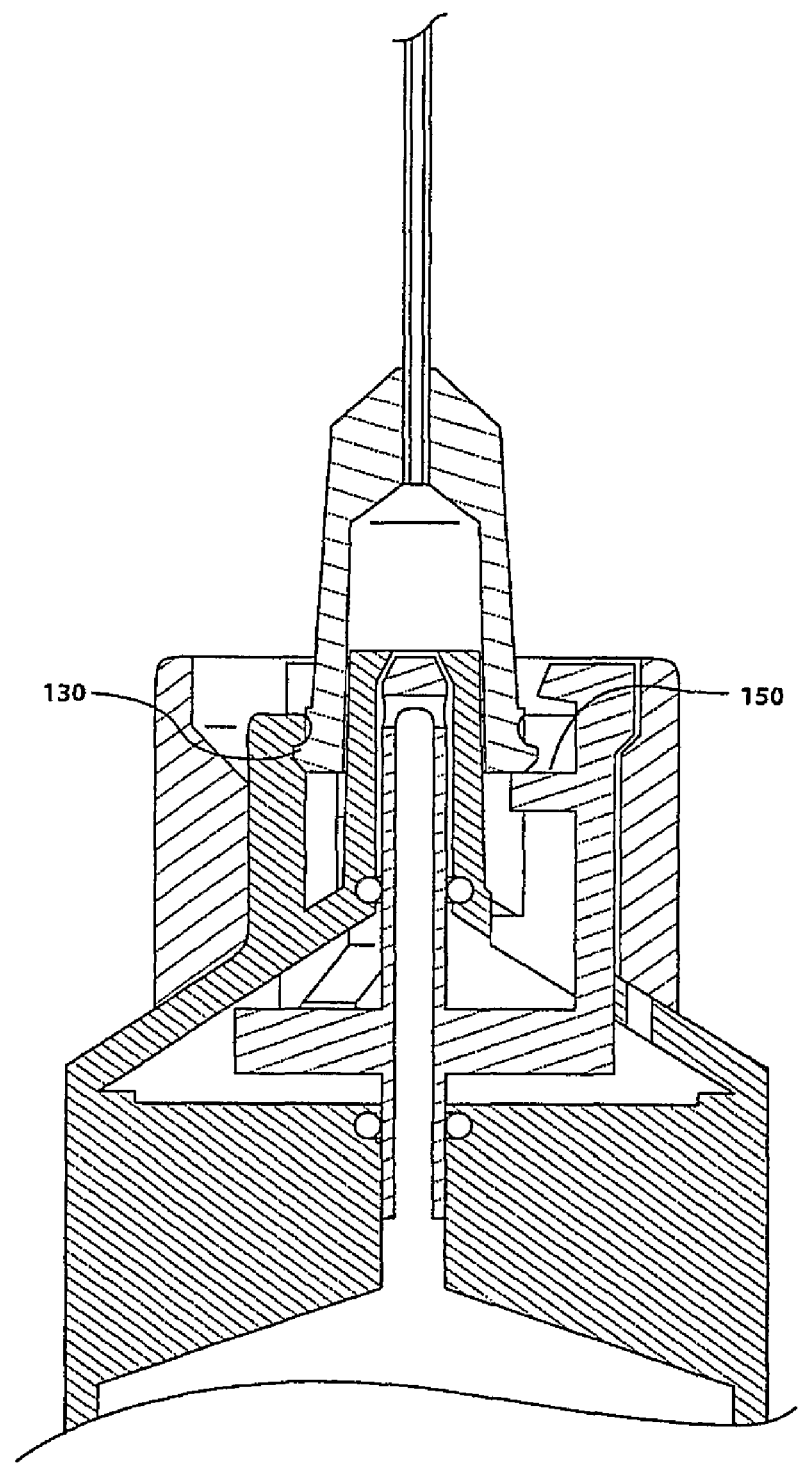

The device 120 is thus used as follows. The valve assembly is set with the valve member in its closed position, that is with the valve member 134 in its position against the valve seat 136 as shown in FIG. 8. The female coupling member 130 on the needle 132 is aligned with the passage 144 and brought toward the male coupling member 128. The bevelled leading surface 152a on the abutment member 152 aids to centre the female coupling member on the mouth of the passage 144. With the locking flange 154 in the locking seat 156, the female coupling member 130 is able to pass the lowermost edge of the abutment element 152 and continue into the passage 144 until the female coupling member makes contact with the abutment element 150 as seen in FIG. 9. As seen in FIG. 10, continued inward force on the female coupling member is transferred to the abutment element 150 causing the abutment portion 146 to move inwardly along the passage and thus to draw the locking flange 154 from this locked position in the locking seat 156, causing the abutment portion 146 to flex, until the locking flange 154 is removed from the locking seat 156. At this position, it can be seen that the valve member 134 has moved from the valve seat 136 to open the fluid channel 163 to the needle 132.

Figure 11:
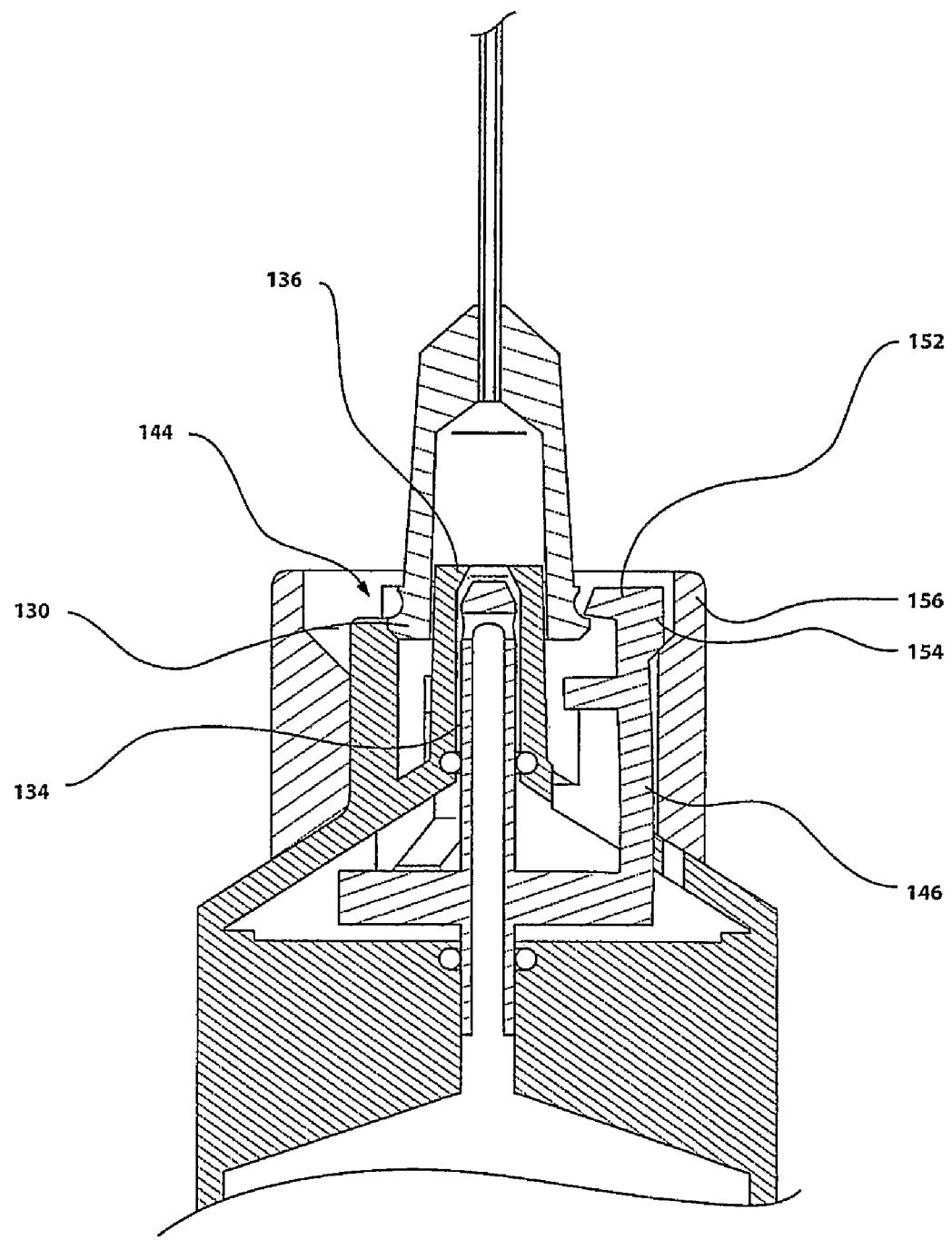
Figure 12:
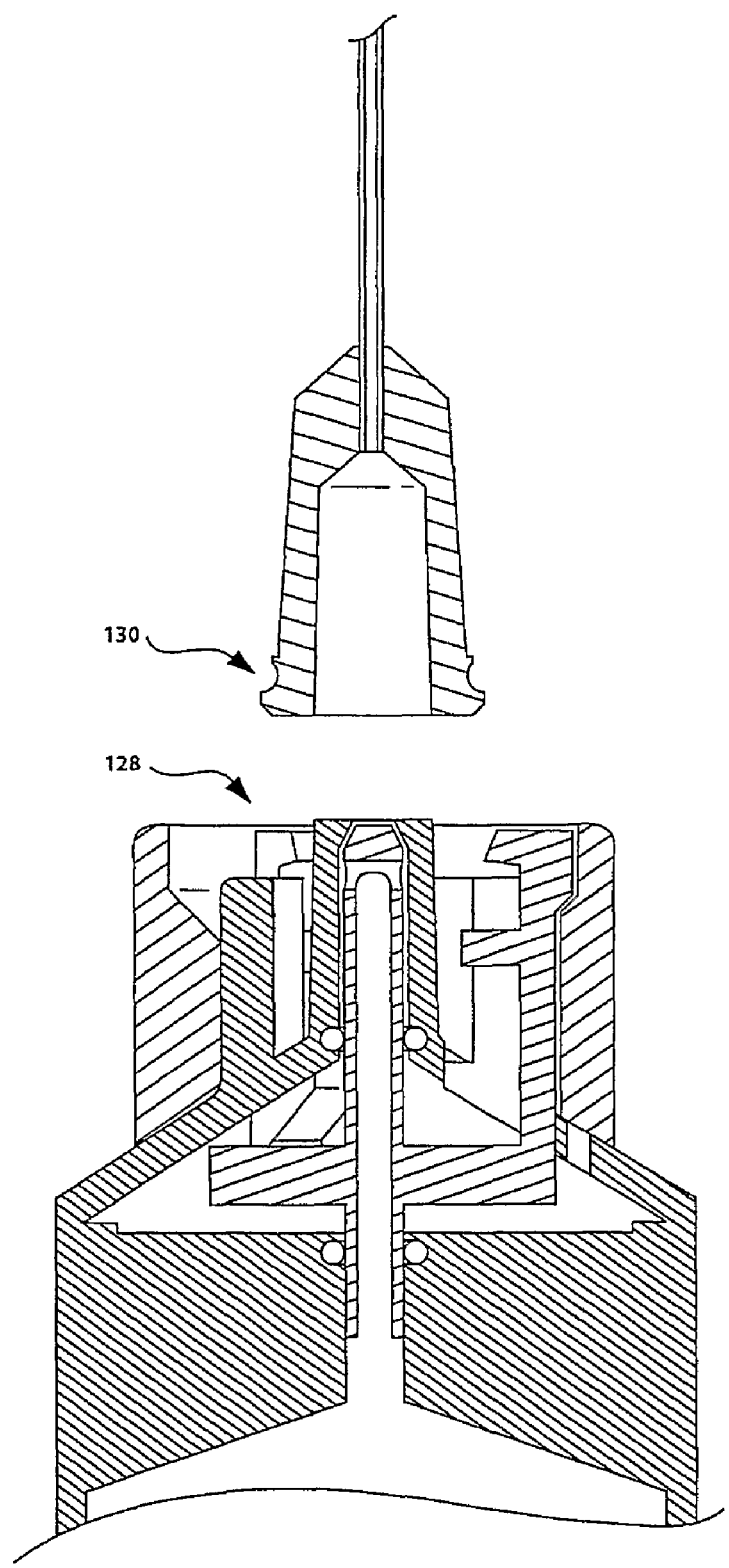

Referring to FIG. 11, as the female coupling member 130 is removed from the passage 144, it makes contact with the abutment element 152 and causes the abutment portion 146 to move outwardly along the passage 144 and thus case the valve member 134 to move toward the valve seat 136. The locking flange 154 approaches, and finally enters, the locking seat 156 to coincide with the closure of the valve assembly.

Thus, the device 120 does not make use of a valve member which is biased to its closed position as with the earlier embodiment, but rather relies on the displacement of the female coupling member 130 to draw the valve assembly to its closed position when it is removed from the male coupling member 128.

Figure 13:
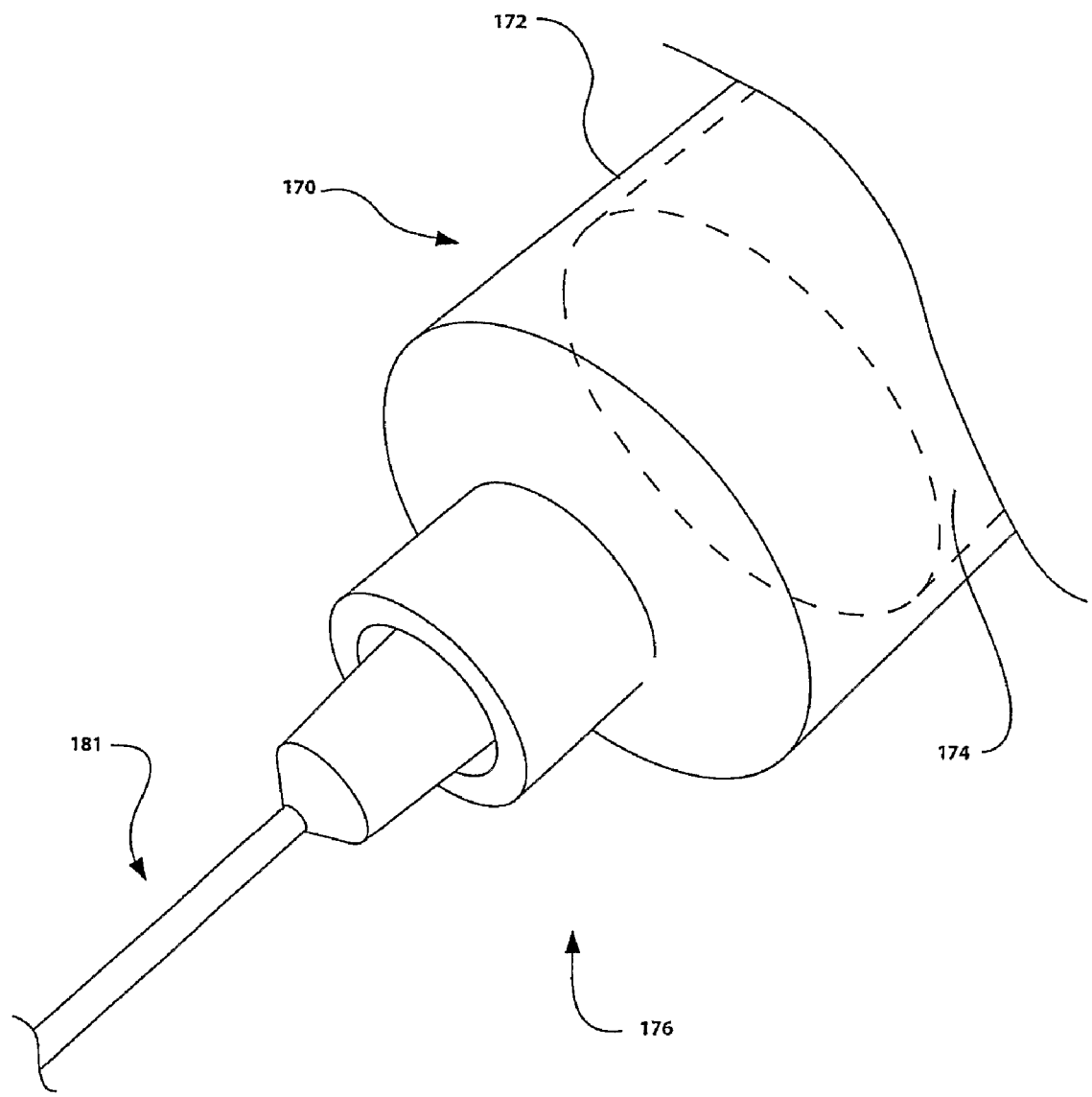
FIG. 13 is a fragmentary perspective view of yet another syringe assembly.
Figure 14:
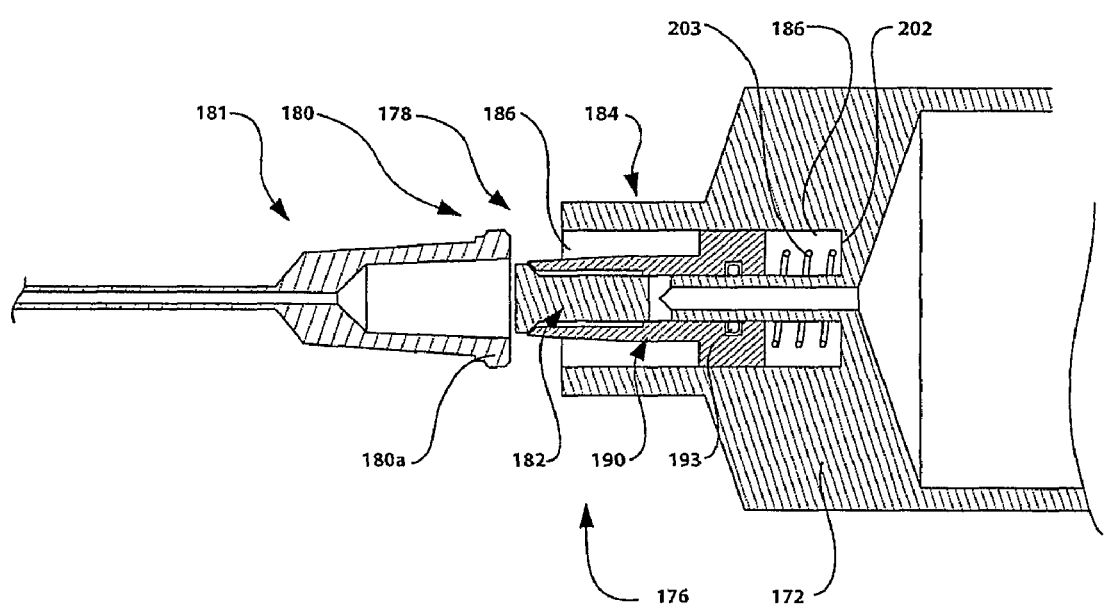
FIGS. 14 and 15 are fragmentary sectional views of the syringe assembly of FIG. 13 or portions thereof.
Figure 15:
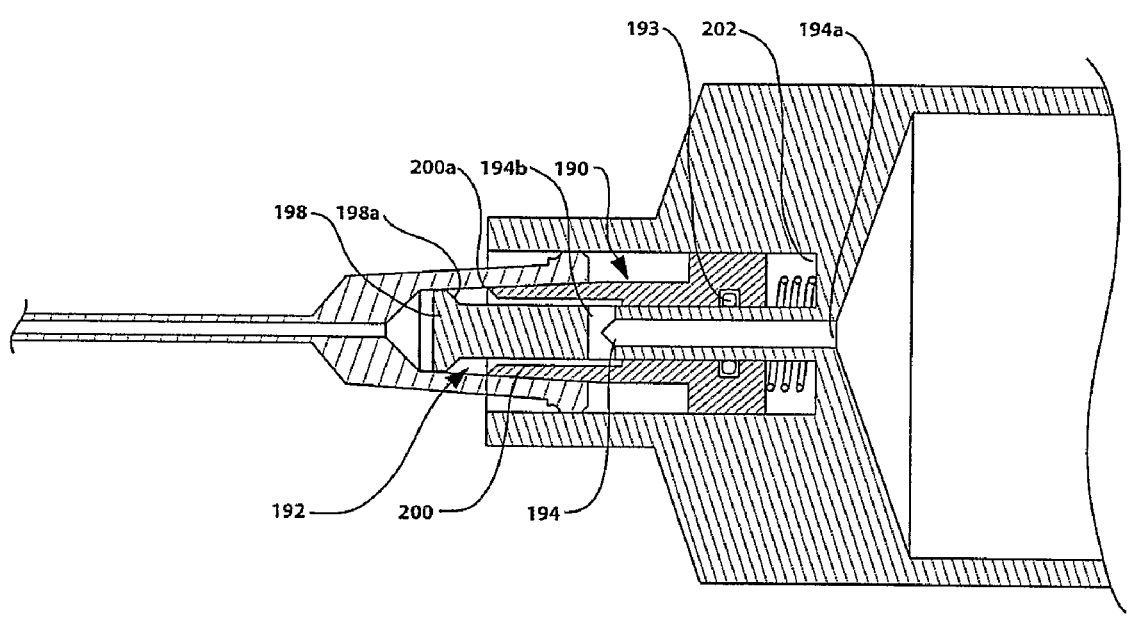

Another device is shown at 170 in FIGS. 13 to 15, having a body 172 providing a chamber 174 therein to contain a fluid material. A valve assembly 176 is in fluid communication with the chamber 174 and has a male coupling member 178 for engaging a female coupling member 180, again on a needle 181, to form a fluid coupling between the medical dispensing device 170 and the needle 181.

The valve assembly 176 is operable to control fluid flow through the male coupling member and more particularly to actuate or open the male coupling member 178 when operatively connected with the female coupling member 180 and, conversely, to close the male coupling member 178 when disconnected from the female coupling member 180.

In this case, the male coupling member 178 includes a projection 182 which is fixed to the body 172. A sheath portion 184 encircles the projection 182 and is also fixed to the body 172. The sheath portion 184 and is spaced from the projection 182 to form a passage 186 to receive the female coupling member 180.

A valve member 190 is movable relative to the projection 182 and forms a fluid channel 192 there between and sealed by an inner seal 193. The projection 182 includes an inner passage 194 which has one end 194a open to the chamber 174 and another end 194b which is open to the fluid channel 192.

Referring to FIGS. 14 and 15, the projection includes an enlarged end portion 198 and the valve member 190 has an outer portion 200 arranged to engage the enlarged end portion 198 to close the fluid channel 192. In this case, the passage 186 ends at an inner wall 202 and the valve member 190 is movable relative to the inner wall 202 under the action of a spring 203 which is positioned in the passage 186 between the valve member 190 and the inner wall 202 to bias the outer end portion 200 of the valve member 190 toward an engaged position with the enlarged end portion 198.

As can be seen in FIG. 15, the enlarged end portion 198 and the outer end portion 200 on the valve member 190 have mating bevelled surfaces 198a and 200a respectively.

The valve member 190 is operable to engage the female coupling member 180 and to travel with the female coupling member 180 along the passage 186. In this case, the female coupling member 180 has a leading segment 180a and the outer end portion 200 of the valve member 190 is dimensioned to fit within the leading segment 180a.

Figure 6:
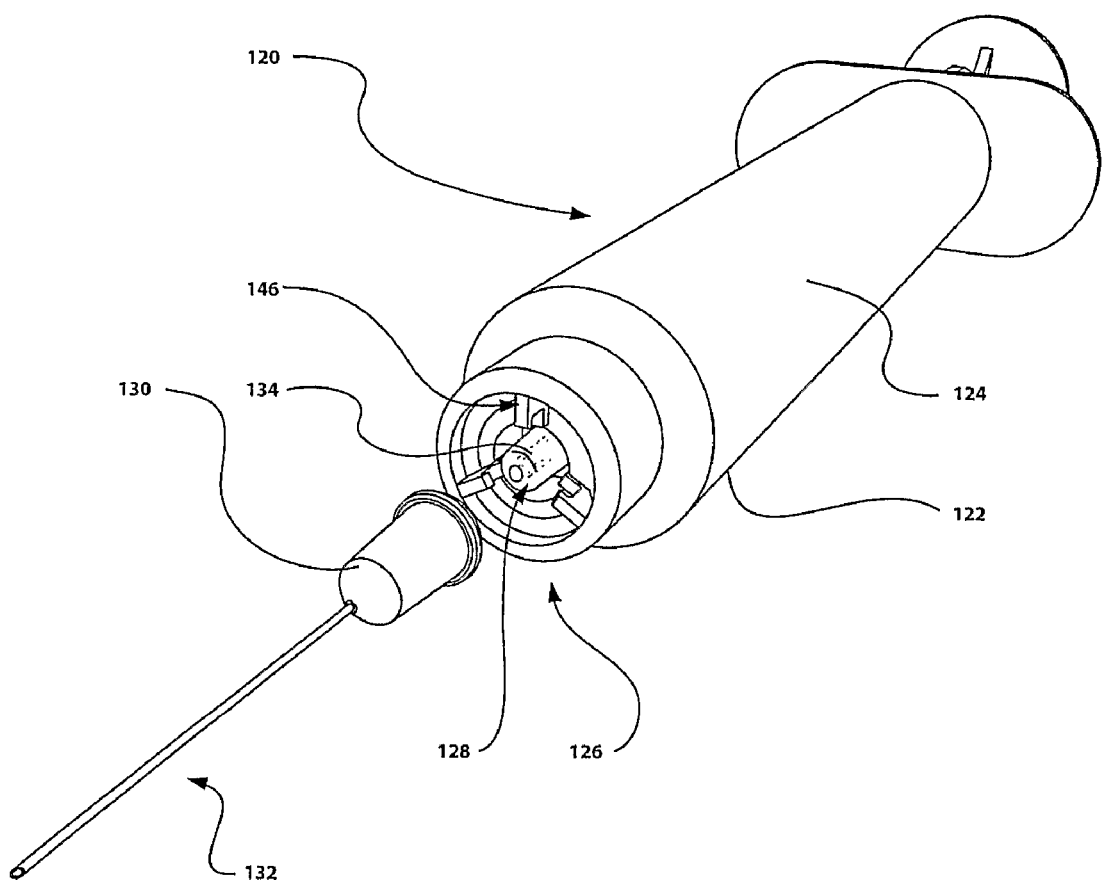
FIGS. 6 and 7 are fragmentary perspective views of another syringe assembly.
Figure 7:
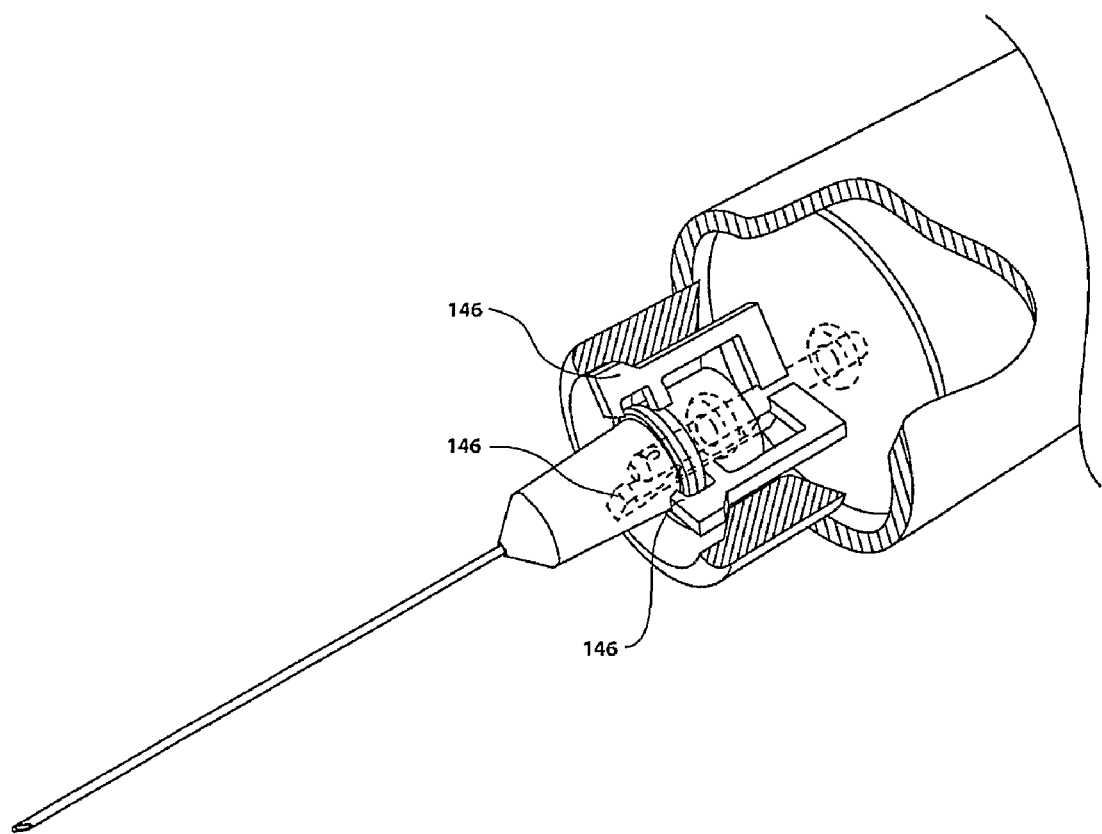

In contrast to the device 120 of FIG. 6, the device 170 has a valve member 190 which is biased to the closed position. As the female coupling member 180 passes over the projection 182, the leading segment 180a of the female coupling member 180 rides over the outer end portion 200 of the valve element 190. Continued inward displacement of the female coupling member 180 into the passage 186 thus causes the valve member to move relative to the projection 182 until the mating bevelled surfaces 198a, 202a separate to open the fluid channel 192 to the needle. The fluid coupling is thus fully operational when the female and male coupling members are tightly engaged. When the female coupling member 180 is removed from the male coupling member 178, the valve member 190 is returned to its closed position against the projection 198 under the biasing action of the spring 203, to close the male coupling member.

While the present invention has been described for what are presently considered the preferred embodiments, the invention is not so limited. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

The valve unit may be used with other medical fluid delivery devices, such as IV lines, catheters, infusion pumps and the like. The valve unit may also be used on syringes and other medical devices which do not employ the ubiquitous luer coupling arrangement.

The invention claimed is:

1. A valved male luer medical connector comprising:

a male luer projection in a distal side of the connector, the male luer projection comprising interior and exterior surfaces and a bore extending between the interior and exterior surfaces, a female luer end portion in a proximal side of the connector, an exterior housing portion positioned between the male luer projection and the female luer end portion, and a fluid passage for the selective passage of fluids within the male luer projection, a region inside of the exterior housing portion, and the female luer end portion, a valve member movable between a closed position and an open position, the valve member comprising a proximal first portion and a second portion distal from the first portion, the first and second portions of the valve member being configured to move generally longitudinally between the closed and open positions such that a proximal end of the first portion is positioned closer to the female luer end portion in the open position than in the closed position, the first portion of the valve member being positioned within the external housing portion between the male luer projection and the female luer end portion in the closed position, and the first portion being positioned outside of the male luer projection in the closed position, and the second portion being positioned at least partially within the male luer projection in the closed position and generally enclosing inside of the second portion at least a portion of a first generally longitudinal fluid pathway and a second generally transverse fluid pathway, the first and second fluid pathways being in fluid communication, the valve member further comprising a plug portion distal from the second portion, the plug portion having a distal end spaced distally from the generally transverse fluid pathway, the plug portion being closed-ended on the distal end thereof in both the open and closed positions such that fluid is prevented from flowing through the distal end of the plug portion in both the open and closed positions, and the plug portion being configured to engage the interior surface of the male luer projection to form a seal such that the closed end of the plug portion is generally flush with a distal end of the exterior surface of the male luer projection in the closed position, a seal contacting the second portion of the valve member, the seal extending generally around a portion of the second portion of the valve member in both the open and closed positions, a biasing member configured to bias the valve member toward the closed position, at least a portion of the biasing member generally surrounding at least a portion of the proximal first portion of the valve member, wherein the biasing member, the valve member, and the seal are discrete, non-unitary components, and an actuating member extending distally into a region near the exterior surface of the male luer projection in the closed position, the actuating member being fixed to and unitary with the valve member, and the actuating member being configured to actuate the valve member from the closed to the open position when a female luer end portion of a medical accessory is advanced into the distal side of the connector, such that fluid is permitted to flow through the generally transverse fluid pathway, around the closed distal end of the plug portion, and through the bore extending between the interior and exterior surfaces of the male luer projection in the open position, and wherein the actuating member, the proximal first portion of the valve member, and the second portion of the valve member are configured to be non-deformable upon contact between the connector and the female luer end portion of the medical accessory.

2. A valved male luer medical connector as defined in claim 1 wherein the distal side of the connector comprises an outer threaded sheath, the actuating member including a portion positioned between the outer threaded sheath and the male luer projection.

3. A valved male luer medical connector as defined in claim 1, wherein the valve member includes an anchor flange extending outwardly toward an inner surface of the housing portion.

4. A valved male luer medical connector as defined in claim 3, wherein the housing portion is coupled to a male luer portion, a portion of the male luer portion comprising the male luer projection, for movement therewith relative to the valve member.

5. A valved male luer medical connector as defined in claim 4 wherein the male luer portion engages the anchor flange when the valve member is in the closed position and the male luer portion is spaced from said anchor flange when the valve member is in the open position.

6. A valved male luer medical connector as defined in claim 5 wherein the housing portion terminates at an end region adjacent the female luer end portion, and the biasing member includes a compression spring located within the housing portion between the end region and the anchor flange.

7. The valved male luer medical connector of claim 1, wherein the valve member further comprises a radially wider portion forming a transition between the first and second portions of the valve member.

8. The valved male luer medical connector of claim 1, wherein the biasing member is a compression spring.

9. The valved male luer medical connector of claim 1, wherein the biasing member does not contact the actuating member or the second portion of the valve member.

10. The valved male luer medical connector of claim 1, wherein the biasing member is contained entirely within an interior region of the connector.

11. The valved male luer medical connector of claim 1, wherein the distal end of the plug portion is narrower than any portion of the second portion of the valve member.

12. The valved male luer medical connector of claim 11, wherein the distal end of the plug portion is narrower than any other portion of the valve member.

13. The valved male luer medical connector of claim 1 wherein the seal is stationary when the valve member moves.

14. The valved male luer medical connector of claim 1 wherein the plug is non-deformable.

15. The valved male luer medical connector of claim 1 wherein the second generally transverse fluid channel pathway consists of side openings on opposing sides of the valve member.

16. The valved male luer medical connector of claim 1 wherein the outer structure of the connector is made of two discrete parts coupled together.

17. The valved male luer medical connector of claim 1 further comprising a second seal positioned near the first proximal portion of the valve member in the open position.

18. The valved male luer medical connector of claim 1 wherein the first proximal portion generally encloses a fluid pathway positioned inside the first proximal portion.

19. The valved male luer medical connector of claim 1 in which the fluid passage is an unimpeded, constantly open fluid passage between the female luer end portion and the region inside the exterior housing.

* * * * *

UNITED STATES PATENT AND TRADEMARK OFFICE
CERTIFICATE OF CORRECTION

PATENT NO. : 7,758,566 B2
APPLICATION NO. : 10/584920
DATED : July 20, 2010
INVENTOR(S) : Simpson et al.

Page 1 of 1

It is certified that error appears in the above-identified patent and that said Letters Patent is hereby corrected as shown below:

In Column 10, Line 20, in Claim 15, after "transverse fluid" delete "channel".

Signed and Sealed this
First Day of March, 2011

David J. Kappos
*Director of the United States Patent and Trademark Office*